United States Patent
Barnes

(10) Patent No.: US 7,090,073 B2
(45) Date of Patent: Aug. 15, 2006

(54) DENTAL TRAY ASSEMBLY

(75) Inventor: Richard Barnes, Sandy, UT (US)

(73) Assignee: Dick Barnes Group, Sandy, UT (US)

( * ) Notice: Subject to any disclaimer, the term of this patent is extended or adjusted under 35 U.S.C. 154(b) by 0 days.

(21) Appl. No.: 10/841,980

(22) Filed: May 6, 2004

(65) Prior Publication Data

US 2004/0238390 A1    Dec. 2, 2004

Related U.S. Application Data

(60) Provisional application No. 60/468,831, filed on May 7, 2003.

(51) Int. Cl.
*A61B 19/02* (2006.01)
*B65D 83/10* (2006.01)

(52) U.S. Cl. ..................... 206/63.5; 206/368

(58) Field of Classification Search ............. 206/63.5, 206/83, 37, 38, 368, 1.5; 220/817, 818, 260, 220/262, 264, 282, 500, 528, 281, 811, 832
See application file for complete search history.

(56) References Cited

U.S. PATENT DOCUMENTS

| | | | |
|---|---|---|---|
| 717,717 A * | 1/1903 | Rowe | 220/264 |
| 2,581,892 A * | 1/1952 | White | 220/573.4 |
| 2,766,902 A * | 10/1956 | Thiele | 220/817 |
| 2,770,387 A * | 11/1956 | Loween | 224/282 |
| 4,227,414 A * | 10/1980 | Elkins | 220/264 |
| 4,694,956 A | 9/1987 | Sims | |
| 4,991,759 A | 2/1991 | Scharf | |
| 4,997,382 A | 3/1991 | Berger | |
| 5,048,731 A | 9/1991 | Moreschini | |
| 5,112,227 A | 5/1992 | Bull | |
| 5,139,188 A * | 8/1992 | Scharf | 224/217 |
| 5,169,315 A | 12/1992 | Bull | |
| 5,249,963 A | 10/1993 | McGarrigle | |
| 5,377,823 A * | 1/1995 | Steen et al. | 206/63.5 |
| D357,409 S * | 4/1995 | Past et al. | D9/423 |
| 5,749,730 A | 5/1998 | Johnsen et al. | |
| 5,823,773 A | 10/1998 | Brysch | |
| 6,182,820 B1 * | 2/2001 | Rathbauer | 206/83 |
| 6,309,222 B1 | 10/2001 | Billingsley | |
| 6,776,166 B1 * | 8/2004 | Mills-Lindsay et al. | 206/260 |

* cited by examiner

*Primary Examiner*—Mickey Yu
*Assistant Examiner*—J. Gregory Pickett
(74) *Attorney, Agent, or Firm*—Thorpe North & Western LLP

(57) ABSTRACT

A dental tray assembly for storage of oral prosthetics includes a base and a cover, associated with the base and being configured to be alternately positioned relative to the base in a first, closed position, and a second, open position. A biasing element interconnects the base and the cover to provide a biasing force between the cover and the base, the biasing force varying with position of the cover relative to the base to provide an attractive force between the cover and the base when the cover is in the first, closed position, and a repellant force between the cover and the base when the cover is in the second, open position. A storage tray is nestable within the base, the storage tray including at least two compartments, each compartment being configured to receive and store an oral prosthetic therein.

12 Claims, 8 Drawing Sheets

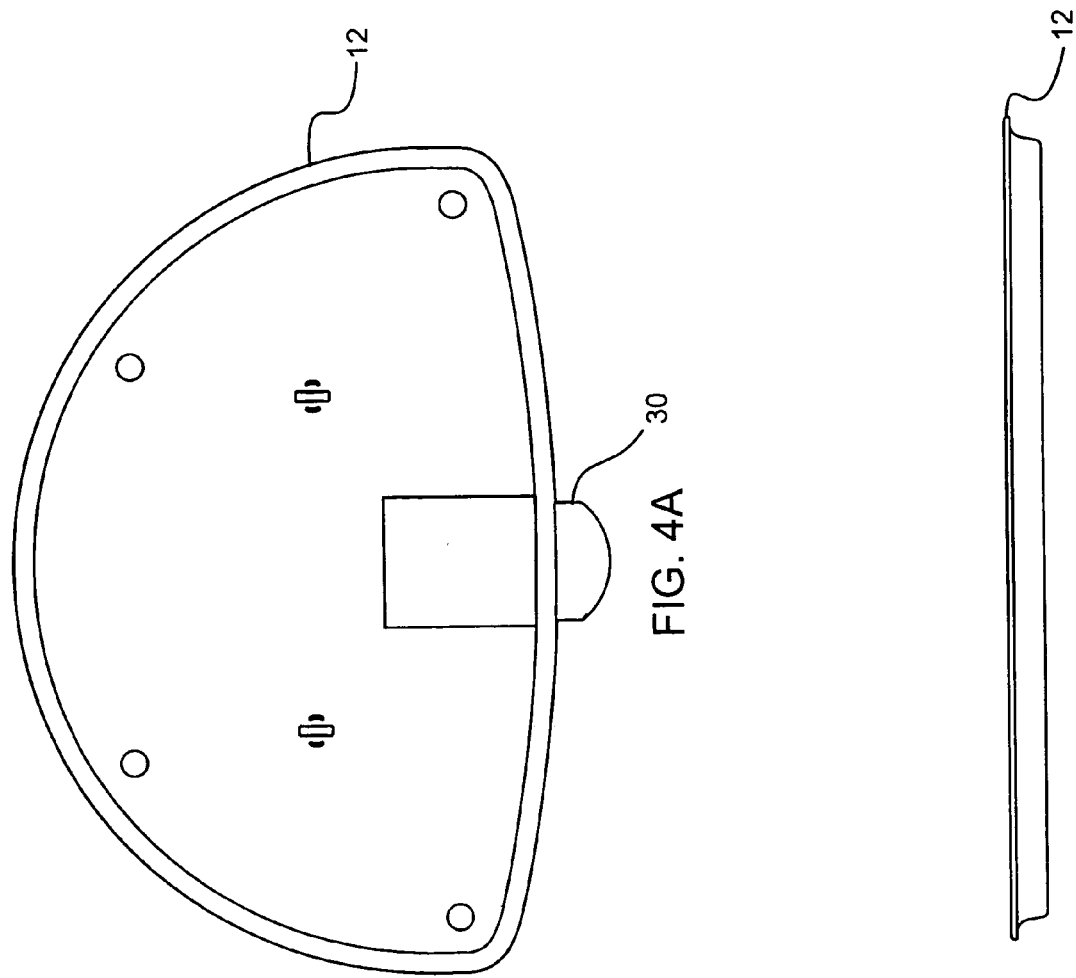

DENTAL TRAY ASSEMBLY

Priority is claimed of U.S. Provisional Application No. 60/468,831, filed May 7, 2003, which is hereby incorporated herein by reference.

BACKGROUND OF THE INVENTION

1. Field of the Invention

The present invention relates generally to a dental tray assembly. More particularly, the present invention relates to a dental tray assembly for the temporary storage of oral prosthetics by dental practitioners.

2. Related Art

Dental practitioners often apply oral prosthetics to dental patients to enhance the appearance of, repair damage to, or replace natural tooth structure. Dental prosthetics can be categorized into two primary types: permanent prosthetics, which are designed to remain on the tooth structure; and removable prosthetics, which can be removed and subsequently replaced by the patient. Removable prosthetics include devices such as dentures, retainers, etc. Examples of permanent oral prosthetics include dental crowns, caps, bridges, orthodontics, etc. In the case where oral prosthetics are applied permanently, the prosthetic is generally bonded or adhered onto or over the tooth structure being treated to ensure that the prosthetic does not become dislodged from the tooth structure over time. For example, dental crowns are generally bonded over a tooth that has been reduced in size prior to application of the crown to thereby give the appearance that the crown is the original tooth. The crown is generally bonded to the tooth structure in order to withstand the forces applied to the crown when the patient eats, flosses, drinks, chews gum, etc.

Because many oral prosthetics must be customized to accurately fit on or over the tooth structure being treated, the prosthetics are generally fabricated by a laboratory, often located off-site of the dental offices where the patient is treated. Thus, the prosthetic is often shipped from the lab to the dental office, where the dental practitioner must identify which patient the prosthetic is for and on which tooth or in which area of the mouth the prosthetic will be attached. Because of the small nature and aesthetic qualities of dental prosthetics, marking identification information directly on the prosthetics is generally not done. Instead, the prosthetic is generally only identified by the package in which the prosthetic is being transported or stored. This makes identification of oral prosthetics difficult without carefully maintaining each prosthetic in its particular package.

In addition to the problems inherent in tracking the identity of oral prosthetics, problems also arise during application of oral prosthetics due to the adhesive that is generally applied to the prosthetic prior to attaching or bonding the prosthetic to the tooth structure. In some applications, the prosthetic is prepared concurrently with preparation of the tooth structure onto or over which the prosthetic is to be applied. In one exemplary scenario, the dental practitioner will first prepare the prosthetic for bonding by applying an adhesive to the prosthetic and then set the "wet" prosthetic aside while the tooth structure is prepared. Once preparation of the tooth structure is complete, the wet prosthetic can be retrieved and placed onto the tooth structure and the bonding process can be finalized. As the adhesive material on the prosthetic must be kept clean from contaminates, placing the wet prosthetic aside can be problematic in that the adhesive may become contaminated while the prosthetic is set aside. Also, excess adhesive may fall or drip from the prosthetic and contaminate otherwise clean surfaces in the dental office.

In addition, many of the adhesives used to bond oral prosthetics are permanently cured by intentionally exposing the adhesive to an ultraviolet ("UV") or other light source once the prosthetic is in place on the tooth structure. If the "wet" prosthetic is allowed to sit for too long in an environment in which it is exposed to natural or artificial light, the adhesive may begin curing prematurely due to the UV content of the natural or artificial light. This can result in a poor bond being formed between the prosthetic and the tooth structure, as the adhesive is partially cured prior to being placed in contact with the tooth structure.

The problems discussed above are further exacerbated when multiple prosthetics are to be applied to a patient in a single visit or sitting. For instance, maintaining identification of an oral prosthetic becomes even more difficult when multiple prosthetics are to be applied to a particular patient at one sitting, as the prosthetics may appear very similar to each but will only correctly fit the particular tooth for which they were tailored. Thus, when multiple prosthetics are to be applied, multiple containers must often be used to aid in tracking the identity of each prosthetic prior to applying the prosthetic to the appropriate tooth structure.

In addition, the most efficient manner to apply multiple prosthetics at one sitting is to prepare all of the prosthetics for bonding (i.e., apply adhesive to the prosthetics), prepare all of the tooth structures to be treated, and then sequentially apply and bond each prosthetic in its appropriate location. However, by doing so, the dental practitioner risks losing track of which of the prosthetics correspond to which tooth, risks contaminating the adhesive, and risks inadvertently beginning the cure of the adhesive by prematurely exposing the adhesive to natural or artificial UV sources. Due to such risks, multiple prosthetics are often prepared and applied one at a time, which results in a great loss of efficiency in the overall process.

SUMMARY OF THE INVENTION

It has been recognized that it would be advantageous to develop a dental tray assembly that can be used to temporarily store oral prosthetics while maintaining identification of each prosthetic. In addition, it has been recognized that it would be advantageous to develop a dental tray assembly that can temporarily store oral prosthetics while protecting adhesive on the prosthetics from contamination and from premature curing due to UV light exposure.

The invention provides a dental tray assembly for storage of oral prosthetics and can include a base, and a cover, associated with the base and being configured to be alternately positioned relative to the base in a first, closed position, and a second, open position. A biasing element can interconnect the base and the cover to provide a biasing force between the cover and the base. The biasing force can vary with position of the cover relative to the base to provide an attractive force between the cover and the base when the cover is in the first, closed position, and a repellant force between the cover and the base when the cover is in the second, open position. A storage tray can be nestable within the base and can include at least two compartments, each compartment being configured to receive and store an oral prosthetic therein.

In accordance with another aspect of the invention, a dental tray assembly for storage of oral prosthetics is provided and can include a base, and a cover, associated with the base and being configured to be alternately positioned relative to the base in a first, closed position, and a second, open position. A substantially rigid linkage member can be pivotally coupled to each of the base and the cover to facilitate movement of the base away from the cover. A biasing element can interconnect the base and the cover to provide a biasing force between the cover and the base. The biasing force can vary with position of the cover relative to the base to provide an attractive force between the cover and base when the cover is in the first, closed position, and a repellant force between the cover and the base when the cover is in the second, open position.

In accordance with another aspect of the invention, a dental tray assembly for storage of oral prosthetics is provided and can include a base, and a cover, associated with the base and being configured to be alternately positioned relative to the base in a first, closed position, and a second, open position. A biasing element can interconnect the base and the cover to provide a biasing force between the cover and the base. The biasing force can vary with position of the cover relative to the base to provide an attractive force between the cover and base when the cover is in the first, closed position, and a repellant force between the cover and the base when the cover is in the second, open position. A ballast can be nested within the base to provide a stabilizing weight within the base to facilitate movement of the cover between the first and second positions without tipping of the tray assembly.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 4A is a top view of a base of a dental tray assembly in accordance with one aspect of the invention;

FIG. 4B is a front view of the base of FIG. 4A;

DETAILED DESCRIPTION

Figure 1A:
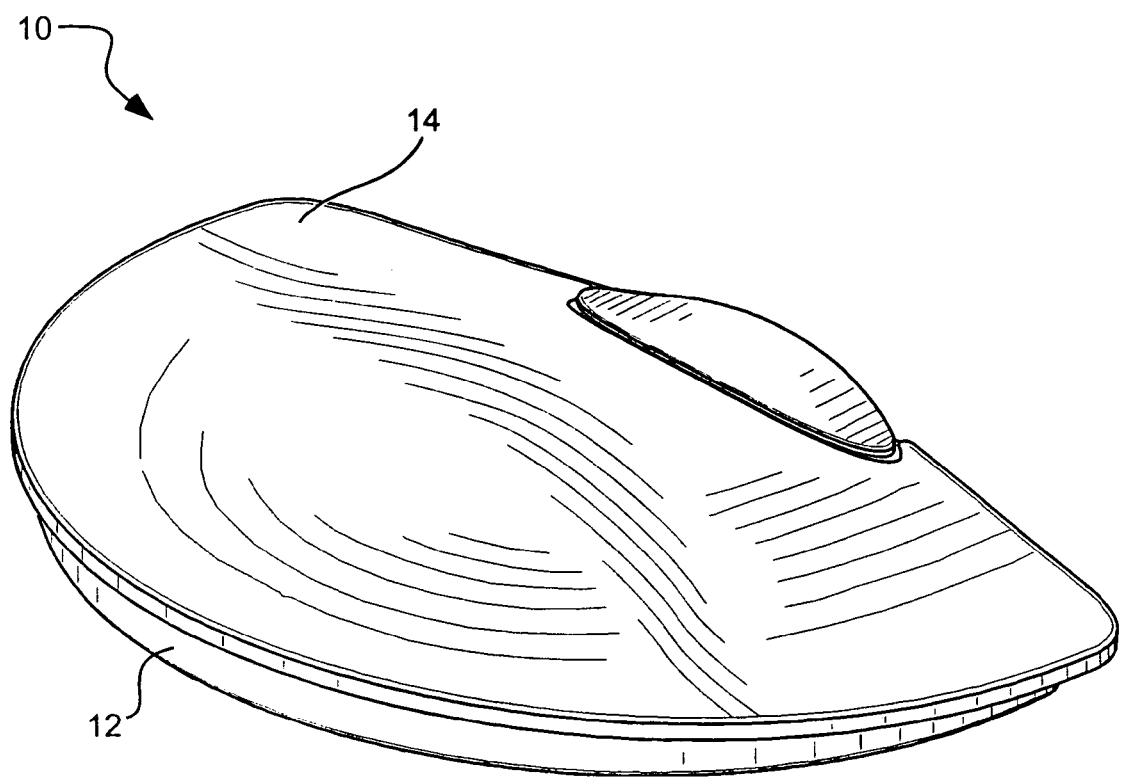
FIG. 1A is a perspective view of a dental tray assembly in a closed position in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 1B:
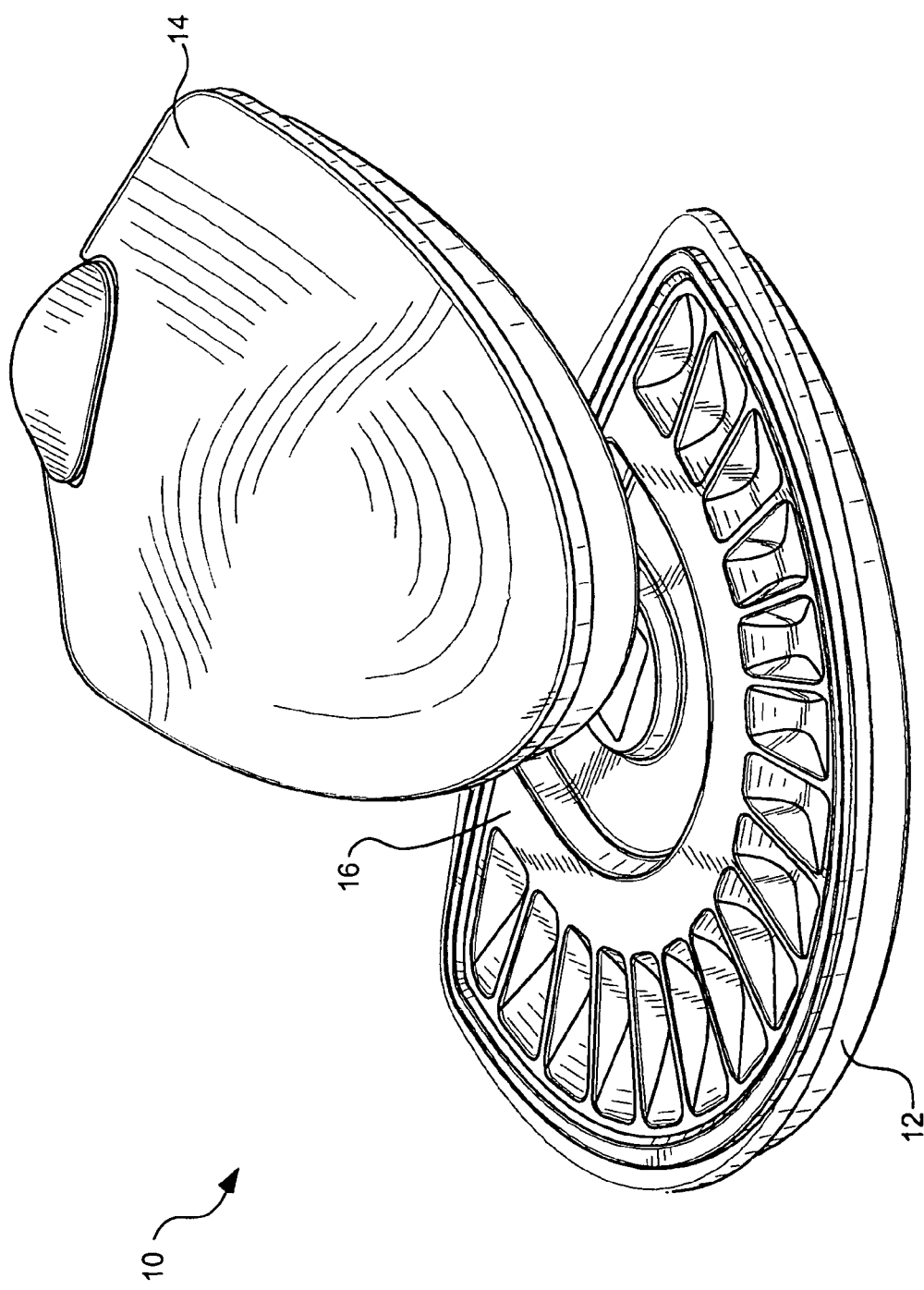
FIG. 1B is a perspective view of the dental tray assembly of FIG. 1A in an open position.

As illustrated in FIGS. 1A and 1B, a dental tray assembly, indicated generally at 10, is provided in accordance with one aspect of the present invention. The assembly is shown in FIG. 1A in a first, closed position and the assembly is shown in FIG. 1B in a second, open position. The assembly generally includes a base 12 and a cover 14. As described in more detail below, the cover and the base can be hingedly coupled to each other to enable opening and closing of the cover relative to the base. The assembly can include a storage tray 16, which, as described in more detail below, can include a plurality of compartments each configured to receive and store an oral prosthetic (not shown) in an identifiable position.

The present invention can be advantageously used by dental practitioners to store and organize a plurality of dental prosthetics in storage tray 16 which can be nested in the base 12. The cover 14 can be used to cover the base and the storage tray, and hence the oral prosthetics stored in the storage tray, to protect the oral prosthetics from contamination due to dirt, dust, etc.; and also to limit exposure of the prosthetics to UV light sources, which can prematurely accelerate the cure of adhesives placed on the prosthetics. As described in more detail below, the present invention provides a dental tray assembly that presents an aesthetically pleasing appearance and can be opened and closed by a dental practitioner with one hand. This advantageously allows the practitioner to operate the dental tray assembly with one hand while leaving the other hand free to perform other tasks associated with the dental procedure being undertaken.

As used herein, the term "oral prosthetic" is meant to include a wide array of dental prosthetics that are applied by a dental practitioner. Examples of oral prosthetics include, but are not limited to, dental crowns, caps, bridges, orthodontic devices, etc. Similarly, the present invention can be used by any number of dental practitioners, including dentists, orthodontists, dental technicians, etc. The dental tray assembly 10 disclosed herein can be formed of a number of materials. In one embodiment, the dental tray assembly is formed of a material which is capable of being autoclaved or otherwise sterilized. The dental tray assembly, in particular, the cover and the base, can be formed of a material that is substantially opaque, to prevent or limit exposure of oral prosthetics contained in the dental tray assembly to UV or other light.

Figure 2:
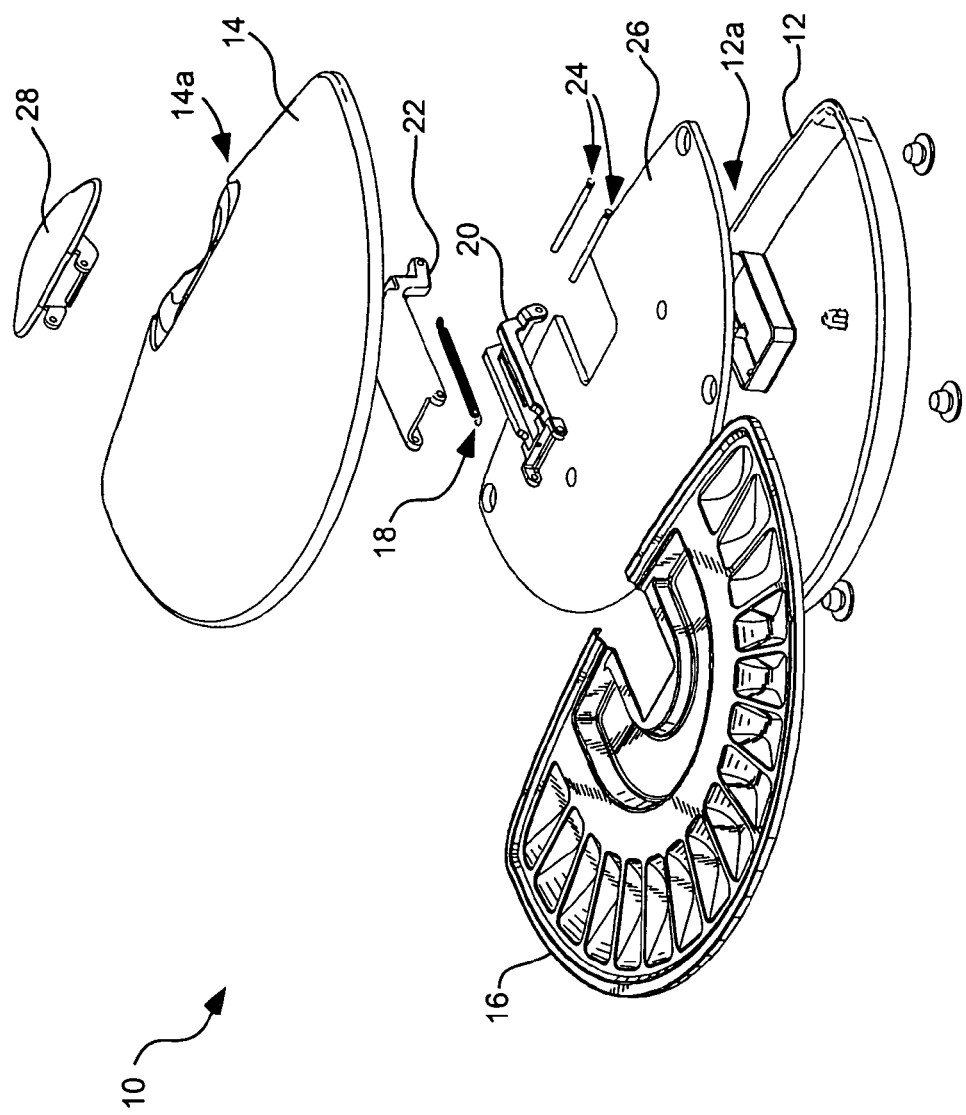
FIG. 2 is an exploded perspective view of the dental tray assembly of FIG. 1A.

FIG. 2 illustrates the various components of the assembly in exploded view. In addition to the base 12, the cover 14 and the storage tray 16, the assembly can include a biasing element 18 which can interconnect the base and the cover. The biasing element can provide a biasing force between the cover and the base to assist in both opening of the cover and maintaining closure of the cover, as dictated by the position of the cover relative to the base. In one aspect, the biasing element provides a biasing force between the base and the cover that varies from an attractive force when the cover is in a first, closed position and a repellant force when the cover is in a second, open position.

As used herein, the term "attractive force" is to be understood to include a force that tends to bias two or more elements toward each other. Thus, the attractive force applied between the cover 14 and the base 12 when in a closed position tends to maintain the closed position, and a degree of force (however small in magnitude) is required to open the cover with respect to the base. Similarly, when in the open position, the biasing element provides a repellent force between the cover and base such that a degree of force (however small in magnitude) is required to move the cover toward the closed position. While the biasing element shown in FIG. 2 is a cylindrical spring, it is to be understood that a variety of biasing elements known to those skilled in the art can also be used. For instance, the biasing element can be a biased cantilever, a leaf spring, a plurality of smaller springs, etc., as would occur to one skilled in the art.

Also shown in FIG. 2 (and schematically in FIGS. 7A through 7B) are lower 20 and upper 22 substantially rigid linkage members that can be pivotally coupled to both the base 12 and the cover 14. The lower and upper linkage members can facilitate pivotal or hinged movement of the cover relative to the base. The biasing element 18 can be coupled between the lower 20 and upper 22 linkage members to operatively provide the biasing force between the cover 12 and the base 14. The linkage members 20, 22 can be pivotally coupled to the base 12 and cover 14 in a variety of manners known to those in the art, including via pins 24, which can be inserted through the respective linkage members and the base and cover.

Figure 5B:
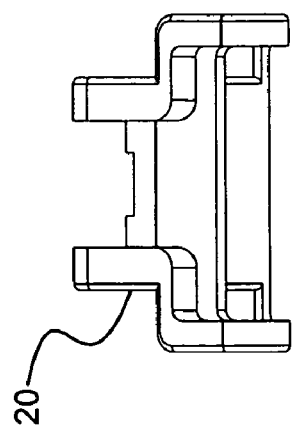
FIG. 5B is an end view of the a lower linkage member of FIG. 5A.
Figure 5C:
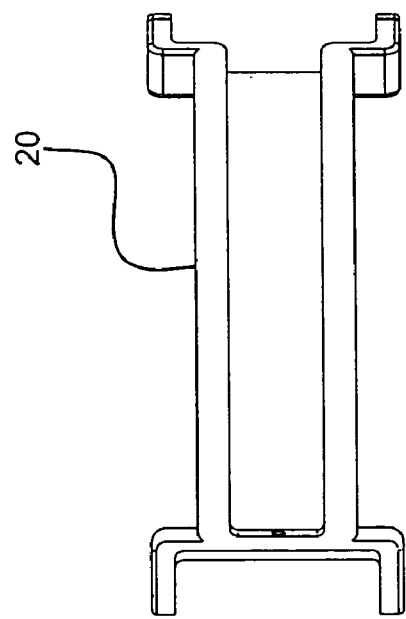
FIG. 5C is a top view of the a lower linkage member of FIG. 5A.
Figure 5A:
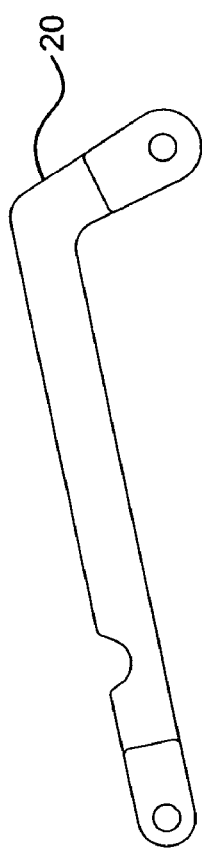
FIG. 5A is a side view of a lower rigid linkage member in accordance with one embodiment of the invention.
Figure 6B:
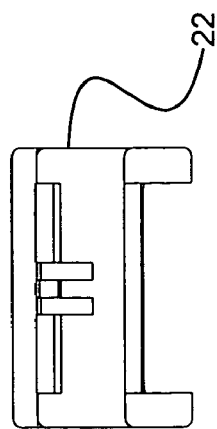
FIG. 6B is an end view of the upper linkage member of FIG. 6A.
Figure 6C:
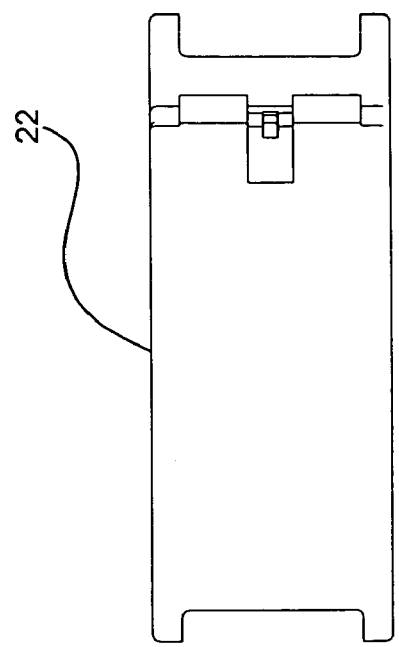
FIG. 6C is a top view of the upper linkage member of FIG. 6A.
Figure 6A:
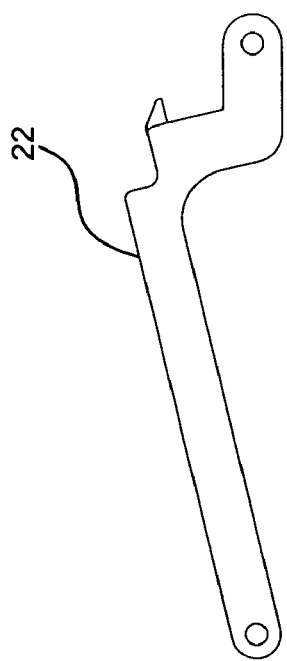
FIG. 6A is a side view of an upper rigid linkage member in accordance with one embodiment of the invention.

In one aspect of the invention, the lower 20 and upper 22 linkage members are pivotally coupled to the base 12 adjacent a rear edge 12a of the base. In this manner, the cover 14 pivots relative to the base such that the cover moves backward and away from the storage space provided by the base. Despite the rearward hinging of the cover, however, the assembly is configured to be physically stable regardless of the position of the cover relative to the base. This feature of the invention is facilitated by the relative position of the lower and upper linkage members, in combination with the biasing element 18. The lower linkage member, when in its most upright position, can serve as a stop for the cover 14 when the cover is in the open position. The lower linkage member is shown in side, end and top view in FIGS. 5A, 5B and 5C, respectively, and the upper linkage member is shown in side, end and top view in FIGS. 6A, 6B and 6C, respectively.

Figure 7A:
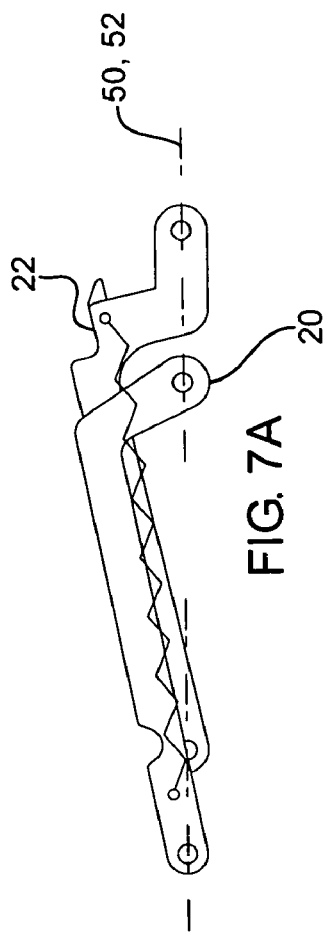
FIG. 7A is a schematic side view of an upper and lower linkage member in accordance with one embodiment of the invention, corresponding to the dental tray assembly being oriented in a first, closed position.
Figure 7C:
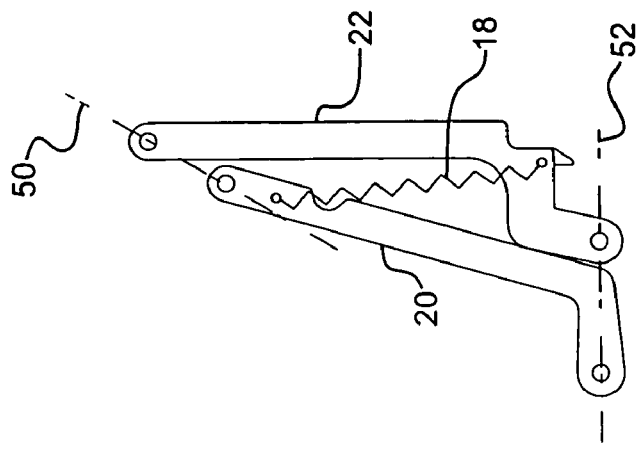
FIG. 7C is a schematic side view of the upper and lower linkage members of FIG. 7A, corresponding to the dental tray assembly being oriented in a second, open position.
Figure 7B:
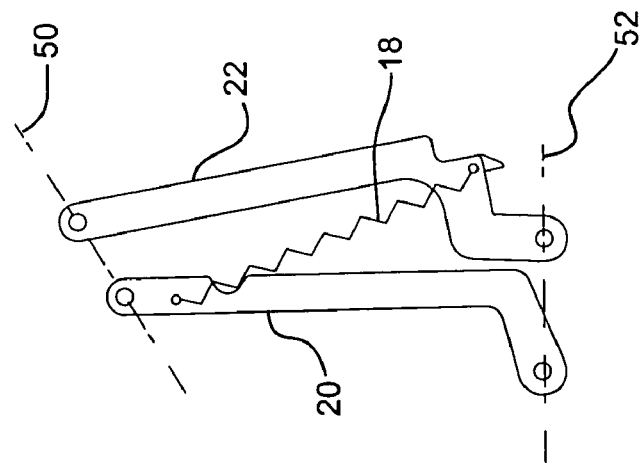
FIG. 7B is a schematic side view of the upper and lower linkage members of FIG. 7A, corresponding to the dental tray assembly being oriented in an intermediate position.

FIGS. 7A through 7C illustrate one exemplary sequence of positions of the dental tray assembly, where axis 50 represents position of the cover (not shown) and axis 52 represents position of the base (also not shown). In FIG. 7A, the cover and base are in the first, closed position with each axis 50, 52 being substantially level with horizontal. As the cover is moved relative to the base, the lower 20 and upper 22 linkage members cooperate with biasing element 18. In one embodiment, as shown in FIG. 7B, the biasing element is most extended, and thus applies the most force, when the cover is in a position intermediate the closed and open positions, as represented by axes 50 and 52. Thus, as the cover moves from the closed position to the open position, the linkage members and biasing element shift the biasing force applied between the cover and base to a repellant force in order to hold the cover open. The cover and base are shown in the open position in FIG. 7C, where it will be appreciated that cover axis 50 is approaching vertical.

It will be appreciated that, in addition to the advantages provided by the one-handed operation of the assembly, the assembly presents an aesthetically pleasing appearance throughout the various stages of opening and closing of the cover, as the front, ornamental face of the cover is continually displayed regardless of the position of the cover. Thus, the various linkage members, biasing elements, pins, etc., remain substantially hidden from view in both the closed and open position of the cover, and during movement of the cover intermediate the closed and open positions.

Returning now to FIG. 2, in one aspect of the invention the dental tray assembly can include a ballast 26 which can be nestable or otherwise associated with the base 12. The ballast can serve to increase a weight of the base to provide stability to the dental tray assembly. While the ballast shown in FIG. 2 includes a generally planar plate corresponding to the general shape of the base, the ballast can be of a variety of sizes and shapes and can be concentrated in a particular location on or within the base to optimize the stability of the assembly as a whole. The ballast can aid in stabilizing the dental tray assembly when the cover 14 is moving between the first, closed position and the second, open position. In addition, the ballast can aid in stabilizing the tray assembly when the cover is in the second, open position, that is, when the tray is in use and may be subject to contact or movement by the dental practitioner.

As also shown in FIG. 2, the dental tray assembly can include latching means 28 which enable the cover 14 to be latched to the base 12 when the cover is in the closed position. The latching means can be of a variety of types known to those skilled in the art and can be disposed in a variety of locations relative to the cover and tray. For instance, the latching means can include "snap," or friction fit, devices, hook mechanisms, etc. In one embodiment, the latching means 28 can be disposed adjacent to rear edges 12a and 14a, respectively, of the base and cover to enable the base and cover to latch together at the rear of the tray assembly.

A separation tab 30 (shown most clearly in FIG. 4A) can be advantageously disposed adjacent to the latching means 28 and can extend outwardly from the base 12. The separation tab can assist a user in operating the latching means with one hand. Thus, a user can place, for instance, his or her middle finger on the separation tab 30 and manipulate the latching means 28 with his or her other fingers or thumb. The cover 14 of the assembly can thereby be easily separated and opened from the base 12 with the use of only one hand, leaving the user's other hand free to perform other tasks. While the separation tab can be utilized to more easily open the cover, it is to be understood that the latching means can be manipulated without engaging the separation tab. The base is shown in front view in FIG. 4B.

The storage tray 16 can be associated with the dental tray assembly to facilitate the organized storage of oral prosthetics (not shown). The storage tray can be formed as an integral portion of the base 12, or the tray can be coupled to or be removable from the base 12. In one embodiment, the storage tray can be nestable within the base and can be formed of a disposable material. In this aspect, the storage tray can be used for one or more procedures and, when contaminated or otherwise unusable, can be discarded and replaced with a clean storage tray. The removable storage tray may be supplied in a sterile state and used for only one patient. Similarly, the storage tray may be supplied to the lab tasked with forming or making the oral prosthetics, and the lab may store the prosthetics in the appropriate compartment of the storage tray and provide the prosthetics to the dental practitioner already stored and ready to apply to a patient's tooth structure. The storage tray 16 is shown in front view in FIG. 3B.

Advantageously, when prosthetics are prepackaged and sealed in the designated compartment within a storage tray by a dental lab, the prosthetics remain in a sterile, or near sterile, condition until needed for application. In this manner, the conventional steps of i) unpackaging a prosthetic, ii) handling it to determine to which tooth the prosthetic corresponds, and iii) placing the prosthetic in a location where it can be retrieved by the practitioner and/or assistant for fitting and application of adhesive are practically avoided.

Figure 3A:
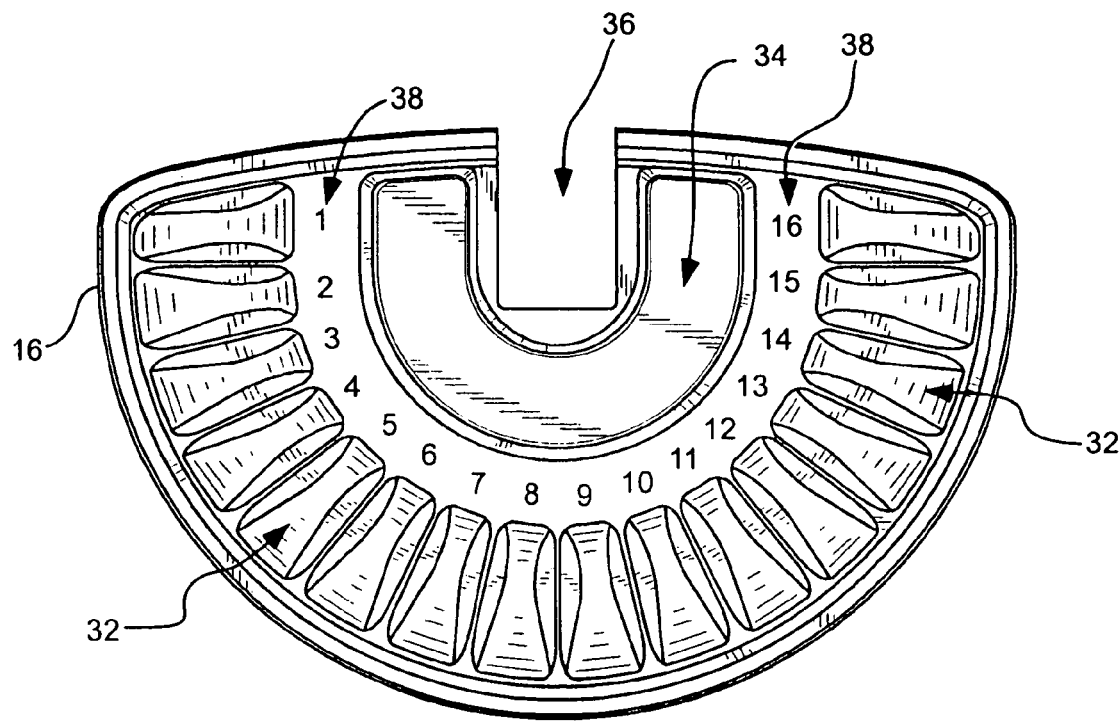
FIG. 3A is a top view of a dental storage tray in accordance with one aspect of the invention.
Figure 3B:
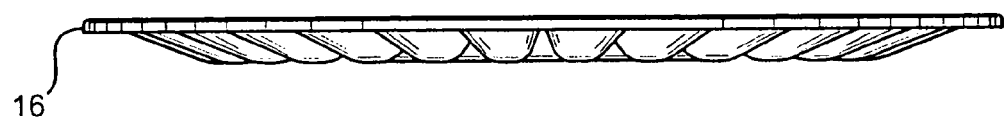
FIG. 3B is a front view of the dental storage tray of FIG. 3A.

As shown in more detail in FIG. 3A, the storage tray 16 can include a plurality of compartments 32 each configured to receive an oral prosthetic (not shown). In addition, a central compartment 34 can be included in the tray to receive and store larger items, such as dental bridge assemblies, which may not otherwise fit in the smaller compartments 32. A notch 36 can be included in the tray to facilitate nesting of the tray around the linkage members (not shown in FIG. 3A) of the dental tray assembly.

A plurality of indicia 38 can be included on the storage tray and can individually correspond to a compartment of the tray to distinguish each compartment of the tray from other compartments. While the indicia can convey a variety of useful reference information, such as alpha-numeric characters, in one embodiment the indicia correspond to tooth numbering of a dental patient. For instance, the indicia shown in FIG. 3A correspond to the permanent teeth numbered 1–16, which is one conventional sequence of numbering corresponding to the teeth in the upper jaw of a human dental patient. In a similar fashion, the indicia could include the sequence of numbers from 17–32, which corresponds to conventional numbering of the permanent teeth in the lower human jaw.

As shown in FIGS. 1A, 3A and 4A, the cover 14, storage tray 16 and base 12 can each include a substantially half-circular shape. By forming the assembly in a half-circular shape, the operative storage space in the base can be maximized while minimizing the space consumed by the substantially rigid linkage members 20, 22, the biasing element 18 and the various pins and coupling points in the cover and the base. In this embodiment, the compartments 32 can be arranged radially about the half-circularly shaped storage tray 16. This arrangement not only provides an accessible and orderly manner of storing oral prosthetics, but also provides an appearance similar to the arrangement of the teeth in a human jaw. This decorative arrangement provides an aesthetically pleasing dental tray storage assembly.

In one embodiment of the invention, not generally illustrated in the figures, the removable storage tray can include a storage tray cover to protect the storage tray and its contents from contaminants, and to retain oral prosthetics in the storage tray during transit of the storage tray. The storage tray cover can include a "snap on" type friction fit, or other attachment means, as known to those in the art. This feature can advantageously allow the removable storage tray to be transported to and from the dental offices and lab to enable organized storage of oral prosthetics in transit.

It is to be understood that the above-referenced arrangements are illustrative of the application for the principles of the present invention. It will be apparent to those of ordinary skill in the art that numerous modifications can be made without departing from the principles and concepts of the invention as set forth in the claims.

What is claimed is:

1. A dental tray assembly for storage of oral prosthetics, including:
   a base;
   a cover, associated with the base and being configured to be alternately positioned relative to the base in a first, closed position, and a second, open position;
   a substantially rigid linkage member, pivotally coupled to each of the base and the cover at different locations on the base and the cover to facilitate movement of the base away from the cover;
   a biasing element, interconnecting the base and the cover, the biasing element being configured to provide a biasing force between the cover and the base, the biasing force varying with position of the cover relative to the base to provide an attractive force between the cover and base when the cover is in the first, closed position, and a repellant force between the cover and the base when the cover is in the second, open position; and
   a storage tray, nestable within the base, the storage tray including at least two compartments, each compartment being configured to receive and store an oral prosthetic therein.

2. The dental tray assembly of claim 1, wherein the substantially rigid linkage member is pivotally coupled to the cover at a first pivot location, and further comprising a second substantially rigid linkage member pivotally coupled to the cover at a second pivot location, the substantially rigid linkage members cooperatively facilitating movement of the cover between the first, closed position and the second, open position.

3. The dental tray assembly of claim 2, wherein one of the substantially rigid linkage members is a rear linkage member and wherein one of the substantially rigid linkage members is a front linkage member, the front linkage member having a shorter operative length than the rear linkage such that a top of the cover is rotated into an exposed condition when the cover is in the second, open position.

4. The dental tray assembly of claim 3, wherein the front linkage member is pivotally coupled to the cover in a position intermediate a front edge of the cover and the rear linkage member.

5. The dental tray assembly of claim 2, wherein the biasing element is coupled between the substantially rigid linkage members.

6. The dental tray assembly of claim 2, wherein the substantially rigid linkage members are each pivotally coupled to the base adjacent a rear edge of the base.

7. The dental tray assembly of claim 1, further comprising latching means, associated with the cover and the base, for enabling latching of the cover and the base when the cover is in the first, closed position, the latching means being disposed adjacent rear edges of the cover and the base to enable one-handed activation of the latching means adjacent the rear edges of the cover and the base.

8. The dental tray assembly of claim 1, wherein the cover and the base are substantially opaque.

9. The dental tray assembly of claim 1, wherein the storage tray is disposable.

10. The dental tray assembly of claim 1, further comprising a ballast, nested within the base, the ballast being configured to provide a stabilizing weight within the base to facilitate movement of the cover between the first and second positions without tipping of the tray assembly.

11. A dental tray assembly for storage of oral prosthetics, including:
- a base;
- a cover, associated with the base and being configured to be alternately positioned relative to the base in a first, closed position, and a second, open position;
- a substantially rigid linkage member, pivotally coupled to each of the base and the cover to facilitate movement of the base away from the cover;
- a biasing element, interconnecting the base and the cover, the biasing element being configured to provide a biasing force between the cover and the base, the biasing force varying with position of the cover relative to the base to provide an attractive force between the cover and base when the cover is in the first, closed position, and a repellant force between the cover and the base when the cover is in the second, open position;
- the substantially rigid linkage member being pivotally coupled to the cover at a first pivot location, and further comprising a second substantially rigid linkage member pivotally coupled to the cover at a second pivot location, the substantially rigid linkage members cooperatively facilitating movement of the cover between the first, closed position and the second, open position.

12. A dental tray assembly for storage of oral prosthetics, including:
- a base;
- a cover, associated with the base and being configured to be alternately positioned relative to the base in a first, closed position, and a second, open position;
- a substantially rigid linkage member, pivotally coupled to each of the base and the cover to facilitate movement of the base away from the cover;
- a biasing element, interconnecting the base and the cover, the biasing element being configured to provide a biasing force between the cover and the base, the biasing force varying with position of the cover relative to the base to provide an attractive force between the cover and base when the cover is in the first, closed position, and a repellant force between the cover and the base when the cover is in the second, open position; and
- latching means, associated with the cover and the base, for enabling latching of the cover and the base when the cover is in the first, closed position, the latching means being disposed adjacent rear edges of the cover and the base to enable one-handed activation of the latching means adjacent the rear edges of the cover and the base.

* * * * *